(12) United States Patent
Schwarz et al.

(10) Patent No.: US 6,277,357 B1
(45) Date of Patent: Aug. 21, 2001

(54) KETOTRICYCLO[5.2.1.0]DECANE DERIVATIVES

(75) Inventors: Michael Schwarz, Gross-Gerau; Ingeborg Stein, Erzhausen; Ulrich Heywang, Darmstadt; Jürgen Eckstein, Rossdorf, all of (DE)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 0 days.

(21) Appl. No.: 08/133,192
(22) PCT Filed: Feb. 2, 1993
(86) PCT No.: PCT/EP93/00234
  § 371 Date: Oct. 19, 1993
  § 102(e) Date: Oct. 19, 1993
(87) PCT Pub. No.: WO93/16978
  PCT Pub. Date: Sep. 2, 1993

(30) Foreign Application Priority Data

Feb. 19, 1992 (DE) .................................................. 42 04 922

(51) Int. Cl.[7] ...................................................... A61K 7/42
(52) U.S. Cl. .......................... 424/59; 514/679; 568/326; 568/313
(58) Field of Search ..................................... 568/324, 373, 568/326, 313; 424/59, 60; 514/679

(56) References Cited

U.S. PATENT DOCUMENTS 3,271,259 * 9/1966 Saunders ............................. 568/373
4,421,729 * 12/1983 Bouillon et al. ...................... 568/327
5,178,852   1/1993 Forestier et al. ....................... 424/60

FOREIGN PATENT DOCUMENTS

| A-0390681 | 10/1990 | (EP) | ...................................... | 424/60 |
| A-2222829 | 3/1990 | (GB) | ...................................... | 424/60 |
| A-2636531 | 3/1990 | (FR) | ...................................... | 424/60 |

* cited by examiner

Primary Examiner—James H. Reamer
(74) Attorney, Agent, or Firm—Millen, White, Zelano & Branigan,

(57) ABSTRACT

The invention relates to ketotricyclo[5.2.1.0]-decane derivatives of the formula I

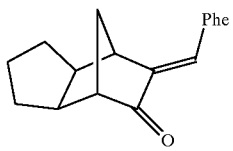

I wherein

Phe is a phenyl group which is unsubstituted or substituted by 1 to 5 hydroxyl, alkyl or alkoxy groups having 1 to 10 C atoms, and their preparation and use as UV filters, in particular in cosmetic or pharmaceutical formulations.

11 Claims, No Drawings

KETOTRICYCLO[5.2.1.0]DECANE DERIVATIVES

This application is a 371 of PCT/EP93/00234 filed on Feb. 2, 1993.

The invention relates to ketotricyclo[5.2.1.0]-decane derivatives of the formula I

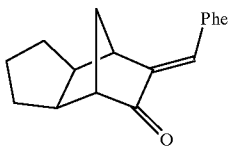

wherein
Phe is a phenyl group which is unsubstituted or substituted by 1 to 5 hydroxyl, alkyl or alkoxy groups having 1 to 10 C atoms,
and to a process for their preparation and their use in cosmetic formulations, in particular for protection from solar radiation, and in pharmaceutical formulations for preventive treatment of inflammations and allergies of the skin or certain types of cancer.

As is known, the skin reacts sensitively to the sun's rays, which can cause common sunburn or erythema, and also more or less severe burns.

However, the sun's rays also have other adverse effects: they cause the skin to lose its elasticity and develop wrinkles and thus lead to premature ageing. Dermatoses can also sometimes be observed. In the extreme case, skin cancer occurs in some people.

It is also desirable to protect hair from photo-chemical damage, in order to prevent changes in color shades, bleaching or damage of a mechanical nature.

It is known that the components contained in cosmetic preparations are not always sufficiently stable to light and decompose under the action of light rays.

As is known, ultraviolet rays with a wavelength of less than 400 nm form the most dangerous part of the sun's rays. It is also known that because of the presence of the ozone layer of the earth's atmosphere, which absorbs some of the solar radiation, the lower limit of the ultraviolet rays which reach the earth's surface is about 280 nm.

It thus appears desirable to provide compounds which can absorb UV rays in a wavelength range of 280 to 400 nm, that is to say also UV-B rays with a wavelength of between 280 and 320 nm, which form a decisive role in the development of solar erythema, and also UV-A rays with a wavelength between 320 and 400 nm, which tan the skin but also age it, promote initiation of an erythematous reaction or intensify this reaction in certain people or can even induce phototoxic or photoallergic reactions.

The sunscreen filters nowadays customary in cosmetics are classified into UVA and UVB filters. While there are good filters in the UVB range (280–320 nm) with substances such as Eusolex® 6300 or Eusolex® 232, those used in the UVA range (320–400 nm) present problems.

Dibenzoylmethanes, such as Parsol® 1789 or Eusolex® 8020, do not have an unlimited stability when exposed to UV irradiation, which on the one hand reduces the effectiveness of the filter in the course of time and on the other hand can promote photosensitizations of the skin in isolated cases. The benzophenones also used as UVA filters have only a limited solubility in the oils used in cosmetics, and they have a relatively low absorption. On the other hand, only a few water-soluble UVA filters are currently known, but their UV absorption is low.

Similar benzylidenecamphor derivatives are known, for example, from EP 0 390 682; however, these do not have a tricyclodecanone structure.

A compound with the designation (+−)-6-oxobenzylidene (3arH.7acH)-5hexahydro-4t.7t-methanoindane, which is embraced by formula I when Phe is unsubstituted phenyl is cited in Beilstein under number BRN=3196309.

Comparison with the original literature cited (H. A. Bruson, T. W. Riener, J. Am. Chem. Soc 67, 1945, 723–28), shows, however, that it is not the 9-benzylidene-tricyclo [5.2.1.0$^{2,6}$]decan-8-one, according to the invention but 3-benzylidenetricyclo[3.3.2.1,$^4$0$^{1,5}$]decan-2-one.

It has been found that ketotricyclo[5.2.1.0]-decane derivatives of the formula I wherein Phe is a phenyl group which is unsubstituted or substituted by 1 to 5 hydroxyl, alkyl or alkoxy groups, in particular an unsubstituted phenyl group, have outstanding UVB filter properties. Their solubility in the oils used in cosmetics is very good, so that use concentrations of up to at least 10% of the formulation are possible even in complicated formulations.

The compounds according to the invention furthermore have an exceptional photostability to UV radiation which by far exceeds the stability of UV filter substances known to date, and are particularly suitable as UVB or UV broad-band filters.

If the extinction in the UVA range has a minimum, this is not a disadvantage, since a UVA filter can be co-incorporated into the formulation without problems.

The compounds of the formula I furthermore can also be used for preventive treatment of inflammations and allergies of the skin and for prevention of certain types of cancer.

In addition to their good properties as filters, the compounds according to the invention are distinguished by a good heat and photochemical stability.

These compounds furthermore offer the advantage of not being toxic or irritating and of being completely harmless to the skin.

They are distributed uniformly in the conventional cosmetic carriers, and can form a continuous film, in particular in fat carriers; they can be applied to the skin in this manner, in order to form an effective protective film.

The invention relates to the compounds of the abovementioned formula I, in particular wherein Phe is unsubstituted phenyl or 1,4-phenyl which is substituted by 1 or 2 alkoxy groups having 1 or 2 C atoms.

Phe is preferably a group of the formula

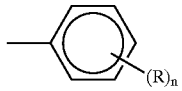

In this formula, R is a methyl, ethyl, n-propyl, i-propyl, n-butyl, i-butyl, t-butyl or 1,1,3,3-tetra-methylbutyl radical, a methoxy, ethoxy or 2-ethylhexyloxy radical or hydrogen, preferably hydrogen.

n is 1 to 5, preferably 1 or 2.

The phenyl group is preferably unsubstituted or substituted by one or two alkoxy groups having 1 to 8 C atoms, in particular by methoxy, ethoxy or 2-ethylhexyloxy groups.

Preferred compounds of the formula I are those of the formulae I1 to I8, wherein A is a group of the formula

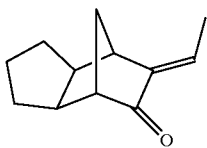

and

R is alkyl or alkoxy having 1 to 10 C atoms.

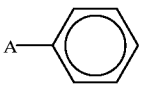

I1

I2

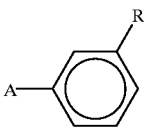

I3

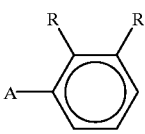

I4

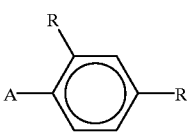

I5

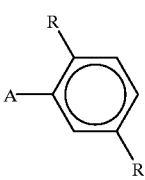

I6

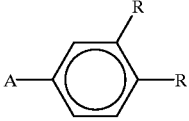

I7

The compounds of the formula I are obtained, for example, by a process in which a benzaldehyde derivative of the formula II

Phe—CHO  II wherein Phe has the meaning given, is reacted with 8-ketotricyclo[5.2.1.0$^{2,6}$] decane in the presence of a base.

The reaction is as a rule carried out in an inert diluent, preferably a protic solvent, in particular an alcohol, such as, for example, methanol, ethanol, isopropanol or tert-butanol, or an aprotic solvent, such as diethyl ether, toluene or cyclohexane, or mixtures of the solvents mentioned. Alkali metal alcoholates, such as, for example, sodium methylate, sodium ethylate or potassium tert-butylate, are preferably employed as the base.

The reaction can be carried out at temperatures between 0° C. and the boiling point of the reaction mixture, and is preferably carried out at 25 to 60° C.

The aldehydes of the formula II are known or are prepared by known methods.

8-Ketotricyclo[5.2.1.0$^{2,6}$] decane is known and is commercially obtainable as an isomer mixture.

The invention also relates to the process for the preparation of the new compounds of the formula I.

The invention furthermore relates to a cosmetic formulation which comprises an active amount of at least one derivative of the above formula I in a cosmetically compatible carrier.

The cosmetic agent according to the invention can be used as an agent for protecting the human epidermis or the hair or as a sunscreen agent.

The invention furthermore relates to a process for protecting the skin and natural or sensitized hair from the sun's rays, an active amount of at least one compound of the formula I being applied to the skin or hair.

"Sensitized hair" means hair which has been subjected to a permanent wave treatment or a dyeing or bleaching process.

The invention furthermore relates to a colored or non-colored light-stabilized cosmetic formulation which comprises an active amount of at least one benzylidene-camphor derivative of the above formula I.

If the cosmetic agent according to the invention is used as an agent for protecting the human epidermis from UV rays, it is present in various forms which are usually used for this type. It can thus be, in particular, in the form of oily or oily-alcoholic lotions, emulsions, for instance as a cream or milk in the form of oily-alcoholic, oily-aqueous or aqueous-alcoholic gels, or as solid sticks, or can be made up as an aerosol.

It can comprise cosmetic adjuvants which are usually used in this type of agent, such as, for example, thickening agents, softening agents, moistening agents, surface-active agents, preservatives, agents which prevent foam formation, perfumes, waxes, lanolin, propellents, dyestuffs and/or pigments, which color the agent itself or the skin, and other ingredients usually used in cosmetics.

The compound of the formula I is as a rule contained in an amount of 0.5 to 10%, preferably 1 to 8%, in particular 1 to 5%, based on the total weight of the cosmetic agent for protection of the human epidermis.

An oil, wax or other fatty substance, a lower monoalcohol or a lower polyol or mixtures thereof can be used as solubilizing agents. The particularly preferred monoalcohols or polyols include ethanol, i-propanol, propylene glycol, glycerol and sorbitol.

A preferred embodiment of the invention is an emulsion which is in the form of a protective cream or milk and comprises, in addition to the compound of the formula I, fatty alcohols, fatty acid esters, in particular triglycerides of fatty acids, fatty acids, lanolin, naturally occurring or synthetic oils or waxes and emulsifiers in the presence of water.

Other preferred embodiments are oily lotions based on naturally occurring or synthetic oils and waxes, lanolin, fatty acid esters, in particular triglycerides of fatty acids, or oily-alcoholic lotions based on a lower alcohol, such as ethanol, or on a glycol, such as propylene glycol, and/or on a polyol, such as glycerol, and oils, waxes and fatty acid esters, such as triglycerides of fatty acids.

The cosmetic agent according to the invention can also be in the form of an alcoholic gel which comprises one or more lower alcohols or polyols, such as ethanol, propylene glycol or glycerol, and a thickening agent, such as silica. The oily-alcoholic gels furthermore comprise naturally occurring or synthetic oil or wax.

The solid sticks comprise naturally occurring or synthetic waxes and oils, fatty alcohols, fatty acid esters, lanolin and other fatty substances.

The invention also relates to cosmetic sunscreen agents which comprise at least one compound of the formula I and can comprise other UVB and/or UVA filters.

In this case, the amount of filter of the formula I is as a rule between 1.0 and 8.0% by weight, based on the total weight of the sunscreen agents.

If an agent is made up as an aerosol, the customary propellents, such as alkanes, fluoroalkanes and chlorofluoroalkanes, are used as a rule.

If the agent according to the invention is to protect natural or sensitized hair from UV rays, it can be in the form of a shampoo, lotion, gel or emulsion for rinsing out, the particular formulation being applied before or after shampooing, before or after dyeing or bleaching or before or after a permanent wave; alternatively, the agent is in the form of a lotion or gel for styling and treatment, in the form of a lotion or gel for brushing or setting a waterwave, or in the form of a hair lacquer, permanent wave agent or dyeing or bleaching agent for hair. In addition to the compound according to the invention, this agent can comprise various adjuvants used in this type of agent, such as surface-active agents, thickening agents, polymers, softening agents, preservatives, foam stabilizers, electrolytes, organic solvents, silicone derivatives, oils, waxes, antiseborrhoeic agents, dyestuffs and/or pigments which color the agent itself or the hair, or other ingredients usually used for hair care. The agent as a rule comprises 1.0 to 5.0% by weight of the compound of the formula I.

The present invention also relates to cosmetic agents which comprise at least one compound of the formula I as agents for protection from UV rays and as antioxidizing agents; these agents include hair products, such as hair lacquers, waterwave lotions for setting the hair, if appropriate for treatment or gentler styling, shampoos, coloring shampoos, hair coloring agents, make-up products, such as nail varnish, creams and oils for skin treatment, foundation, lipsticks, skin care agents, such as bath oils or creams, and other cosmetic agents which can cause problems with light stability and/or oxidation in the course of storage with respect to their components. Such agents as a rule comprise 1.0 to 5.0% by weight of a compound of the formula I.

The invention furthermore relates to a process for protection of cosmetic agents from UV rays and oxidation, an active amount of at least one compound of the formula I being added to these agents.

The invention furthermore relates to the use of the compounds of the formula I as sun filters having a wide absorption span in a wavelength range of 320 to 400 nm.

The invention furthermore relates to the use of the compounds of the formula I as cosmetic products.

As already mentioned above, in the course of its studies, the Applicant Company furthermore has found that the compounds of the formula I have a significant pharmacological activity in the field of preventive treatment of inflammations and skin allergies.

The invention also relates to the compounds of the formula I for use as a medicament.

The invention furthermore relates to a pharmaceutical agent which comprises an active amount of at least one compound of the formula I as the active substance in a non-toxic carrier or excipient.

The pharmaceutical agent according to the invention can be administered orally or topically.

For oral administration, the pharmaceutical agent is present in the form of pastels, gelatin capsules or coated tablets or as a syrup, suspension, solution, emulsion and the like. For topical application, it is present in the form of an ointment, cream, pomade, solution, lotion, gel, spray, suspension and the like.

This agent can comprise inert or pharmacodynamically active additives, in particular hydrating agents, antibiotics, steroid or non-steroid antiinflammatory agents, carotinoids and agents against psoriasis.

This agent can also comprise flavor-improving agents, preservatives, stabilizers, moisture regulators, pH regulators, modifiers for osmotic pressure, emulsifiers, local anaesthetics, buffers and the like.

It can furthermore be conditioned in a manner which is known per se in a retarded form or in a form in which the active compound is released rapidly.

Even without further statements, it is assumed that an expert can utilize the above description in the broadest scope. The preferred embodiments are therefore to be interpreted merely as a descriptive disclosure and in no way as a disclosure which is limited in any manner.

The complete disclosure of all the applications, patents and publications mentioned above and below and the corresponding Application P 42 04 922, filed on 19.02.1992, are introduced into this Application by reference.

The following examples are representative of the present invention.

EXAMPLE 1

9-Benzylidene-8-keto-tricyclo-[5.2.1.0$^{2,6}$] decane

A suspension of 40 mmol (6.3 g) of 8-ketotricyclo [5.2.1.0$^{2,6}$] decane (isomer mixture) and 60 mmol of sodium methylate (10.7 g of a 30% strength solution) in 75 ml of cyclohexane is stirred at 50° C. for 30'. 50 mmol (5.3 g) of benzaldehyde are then added dropwise and the mixture is heated at reflux for 1 hour. Thereafter, the mixture is cooled to room temperature and 175 ml of water are added. The phases are separated and the aqueous phase is extracted with cyclohexane. The combined organic extracts are extracted by shaking with 50 ml of 1N HCl solution, washed neutral with water, dried, filtered and evaporated on a rotary evaporator.

Chromatography with toluene/ethyl acetate 98:2 gave a crude product, which was recrystallized from isopropanol for further purification.

5.94 g=62%;

Melting point: 87.7–88.1° C.

UV (ethanol, c=1 mg/100 ml):2 [sic]$_{max}$=305 nm;

E=0.946 (d=1 cm);

log $\epsilon$=3.60.

The other spectra correspond to the expected compound.

The following are prepared analogously:

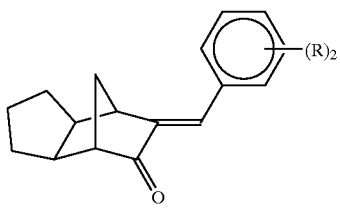

| R | Solvent | Max (nm) | Extinction | log ε | UV |
|---|---|---|---|---|---|
| 2,3-OCH₃ | EtOH | 293.2 | 0.591 | 3.30 | B |
| 2,4-OCH₃ | EtOH | 337.3 | 0.661 | 3.35 | AB |
| 2,5-OCH₃ | EtOH | 353.6 | 0.269 | 2.95 | A |
| 3,4-OCH₃ | EtOH | 329.6 | 0.675 | 3.35 | AB |
| 2,4,6-OCH₃ | EtOH | 326.2 | 0.528 | 3.21 | AB |
| 2,4,5-OCH₃ | EtOH | 359.5 | 0.491 | 3.18 | A |
| 2,3,4-OCH₃ | EtOH | 320.0 | 0.653 | 3.30 | AB |

Solubility of the substances according to the invention

| R, R' | Isopropanol | Miglyol | Paraffin oil | Water |
|---|---|---|---|---|
| H, H | 7.40% | 10.80% | 2.40% | 0.01% |
| 2,3-OCH₃ | 8.57% | 9.64% | 0.91% | 0.01% |
| 2,4-OCH₃ | 0.95% | 1.64% | 0.14% | 0.01% |
| 3,4-OCH₃ | 1.57% | 3.19% | 0.17% | 0.01% |
| 2,4,6-OCH₃ | 0.26% | 0.43% | 0.02% | 0.01% |
| 2,4,5-OCH₃ | 0.04% | 0.07% | 0.03% | 0.01% |
| 2,3,4-OCH₃ | 3.21% | 2.64% | 0.26% | 0.01% |

Photostability of the substances according to the invention

Loss of extinction at $\lambda_{max}$ after irradiation [minutes]

| R, R' | 15 min. | 30 min. | 60 min. | 120 min. | 180 min. |
|---|---|---|---|---|---|
| H, H | 10.00% | 10.00% | 12.50% | 17.50% | 22.50% |
| 2,3-OCH₃ | 12.50% | 12.50% | 14.10% | 17.20% | 18.80% |
| 2,4-OCH₃ | 13.60% | 22.0% | 37.30% | 59.30% | 76.30% |
| 3,4-OCH₃ | 17.50% | 26.30% | 42.10% | 64.90% | 80.70% |
| 2,4,6-OCH₃ | | | 28.80% | | 33.80% |
| 2,4,5-OCH₃ | | | 24.40% | | 61.50% |
| 2,3,4-OCH₃ | | | 30.70% | | 61.30% |

EXAMPLE 2

Sunscreen Cream (water-in-oil)

| | | | % |
|---|---|---|---|
| A | 9-Benzylidene-8-ketotricyclo-[5.2.1.0²,⁶] decane (=BKTD) | (1) | 3.00 |
| | Arlacel 581 | (2) | 7.00 |
| | Highly liquid paraffin (Art. No. 7174) | (1) | 6.00 |
| | Arlamol S 7 | (2) | 2.00 |
| | Lunacera M | (3) | 5.00 |
| | Dow Corning 344 | (4) | 4.00 |
| | Miglyol 812 | (5) | 2.00 |
| | Oxynex 2004 (Art. No. 6940) | (1) | 0.05 |
| B | Glycerol (Art. No. 4093) | (1) | 2.00 |
| | Magnesium sulphate heptahydrate (Art. No. 5882) | (1) | 0.17 |
| | Preservative | | q.s. |
| | Water, demineralized | | to 100.00 |

Preparation

Heat phase A to 75° C. and phase B to 80° C. Stir phase B slowly into phase A. Homogenize. Cool, while stirring. If appropriate, perfume at 40° C.

Sources of supply:

(1) E. Merck, Darmstadt (2) ICI, Essen (3) LW Fuller, Lüneburg (4) Dow Corning, Düsseldorf (5) Hüls Troisdorf AG, Witten

EXAMPLE 3

Sunscreen Cream (oil-in-water)

| | | | % |
|---|---|---|---|
| A | BKTD | (1) | 3.00 |
| | Emulsifier E 2155 | (2) | 8.00 |
| | Stearic acid (Art. No. 671) | (1) | 2.00 |
| | Liquid paraffin (Art. No. 7162) | (1) | 6.00 |
| | Non-caking paraffin (Art. No. 7158) | (1) | 6.00 |
| | Cetyl alcohol (Art. No. 989) | (1) | 2.50 |
| | Miglyol 812 | (3) | 9.50 |
| | Abil AV 200 | (2) | 0.50 |
| | Cetyl palmitate (Art. No. 15419) | (1) | 5.50 |
| | Tocopherol acetate (Art. No. 500952) | (1) | 0.05 |
| B | Glycerol (Art No. 4093) | (1) | 3.00 |
| | Propane-1,2-diol (Art. No. 7478) | (1) | 2.00 |
| | Karion F liquid (Art. No. 2993) | (1) | 5.00 |
| | Allantoin (Art. No. 1015) | (1) | 0.25 |
| | Triethanolamine (Art. No. 8377) | (1) | 0.50 |
| | Preservative | | q.s. |
| | Water, demineralized | | to 100.00 |

Preparation

Heat phase A to 75° C. and phase B to 80° C. Stir phase B slowly into phase A. Homogenize. Cool, while stirring. If appropriate, perfume at 40° C.

Sources of supply:

(1) E. Merck, Darmstadt (2) Th. Goldschmidt, Essen (3) Hüls Troisdorf AG, Witten

EXAMPLE 4

Sunscreen Milk (water-in-oil)

|   |   |   | % |
|---|---|---|---|
| A | BKTD | (1) | 3.00 |
|   | Pionier L-15 | (2) | 19.00 |
|   | Viscous paraffin (Art. No. 7160) | (1) | 15.00 |
| B | Glycerol (Art. No. 4093) | (1) | 5.00 |
|   | Magnesium sulfate heptahydrate (Art. No. 5882) | (1) | 0.50 |
|   | Preservative |   | q.s. |
|   | Water, demineralized |   | to 100.00 |

Preparation

Heat phase A to 75° C. and phase B to 80° C. Stir phase B slowly into phase A. Homogenize. Cool, while stirring. If appropriate perfume at 40° C.

Sources of supply:
(1) E. Merck, Darmstadt
(2) Hansen & Rosenthal, Hamburg

EXAMPLE 5

Sunscreen Milk (water-in-oil)

|   |   |   | % |
|---|---|---|---|
| A | BKTD | (1) | 3.00 |
|   | Eumulgin B 1 | (2) | 3.00 |
|   | Cutina MD | (2) | 8.00 |
|   | Miglyol 812 | (3) | 7.00 |
| B | Glycerol (Art. No. 4093) | (1) | 5.00 |
|   | Preservative |   | q.s. |
|   | Water, demineralized |   | to 100.00 |

Preparation

Heat phase A to 75° C. and phase B to 80° C. Stir phase B slowly into phase A. Homogenize. Cool, while stirring. If appropriate, perfume at 40° C.

Sources of supply:
(1) E. Merck, Darmstadt
(2) Henkel, Düsseldorf
(3) Hüls Troisdorf AG, Witten

EXAMPLE 6

Sunscreen Oil

|   |   |   | % |
|---|---|---|---|
| A | BKTD | (1) | 3.00 |
|   | Arlatone T | (2) | 2.00 |
|   | Miglyol 812 | (3) | 16.00 |
|   | Cetiol B | (4) | 22.50 |
|   | Isopropylmyristate | (4) | 7.50 |
|   | Highly liquid paraffin (Art. No. 4174[sic]) | (1) | 48.85 |
|   | Oxynex 2004 (Art. No. 6940) | (1) | 0.05 |
| b | Perfume oil 72979 | (5) | 0.10 |

Preparation

Heat phase A to 70° C., while stirring, until all the components have dissolved, stir until cold and add phase B at 40° C.

Sources of supply:

(1) E. Merck, Darmstadt
(2) ICI, Essen
(3) Hüls Troisdorf AG, Witten
(4) Henkel, Düsseldorf
(5) Haarmann & Reimer, Holzminden

What is claimed is:

1. A ketotricyclo[5.2.1.0]decane derivative of formula I

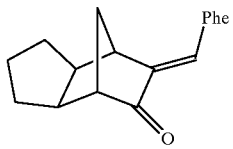

wherein

Phe is a phenyl group which is unsubstituted or substituted by 1 to 5 alkyl or alkoxy groups having 1 to 10 C atoms.

2. Ketotricyclo [5.2.1.]decane derivatives according to claim 1, wherein Phe is a phenyl group which is unsubstituted or substituted by 1 or 2 alkoxy groups having 1 or 2 C atoms.

3. A method for preventing inflammations and allergies of the skin caused by UV irradiation, comprising administering an effective amount of a compound of claim 1.

4. A method of preventing cancer caused by UV irradiation, comprising administering an effective amount of a compound of claim 1.

5. A process for the preparation of a ketotriciclo[5.2.1.0] decane derivative of claim 1, comprising reacting a benzaldehyde compound of formula II Phe—CHO     II wherein Phe has the given meaning, with 8-ketotricyclo[5.2.1.0$^{2,6}$]decane in the presence of a base.

6. A process according to claim 5, wherein the base is an alkali metal alcoholate.

7. A cosmetic formulation, comprising an effective UV radiation-protective amount of a ketotricyclo[5.2.1.0]decane derivative of claim 1 in a cosmetically compatible carrier.

8. A cosmetic for mulation of claim 7, wherein the ketotricyclo[5.2.1.0]decane derivative is present in an amount of 0.5 to 10% by weight of the formulation.

9. A cosmetic formulation of claim 7, further comprising a UV-A filter.

10. A pharmaceutical preparation, comprising an effective UV radiation-protective amount of a ketotricyclo[5.2.1.0] decane derivative of claim 1 and a pharmaceutically acceptable excipient.

11. A pharmaceutical preparation of claim 10, for topical use.

* * * * *

UNITED STATES PATENT AND TRADEMARK OFFICE
CERTIFICATE OF CORRECTION

PATENT NO. : 6,277,357 B1
DATED : August 21, 2001
INVENTOR(S) : Michael Schwarz et al.

It is certified that error appears in the above-identified patent and that said Letters Patent is hereby corrected as shown below:

<u>Column 10, claim 2,</u>
Line 1, reads "[5.2.1.]" should read -- [5.2.1.0] --

<u>Column 10, claim 8,</u>
Line 1, reads "for mulation" should read -- formulation --

Signed and Sealed this

Second Day of April, 2002

Attest:

JAMES E. ROGAN
*Attesting Officer*  *Director of the United States Patent and Trademark Office*